United States Patent [19]

DuRoss

[11] Patent Number: 5,075,291

[45] Date of Patent: Dec. 24, 1991

[54] CRYSTALLINE SUGAR ALCOHOL CONTAINING UNIFORMLY DISPERSED PARTICULATE PHARMACEUTICAL COMPOUND

[75] Inventor: James W. DuRoss, Smryna, Del.

[73] Assignee: ICI Americas Inc., Wilmington, Del.

[21] Appl. No.: 441,131

[22] Filed: Nov. 22, 1989

[51] Int. Cl.$^5$ .......................... A61K 7/00; A23G 1/00; A23G 3/30; C07H 15/08
[52] U.S. Cl. ........................................ 514/60; 514/54; 514/777; 514/778; 514/965; 127/29; 424/48; 424/440; 424/469; 426/3; 426/658
[58] Field of Search ................... 514/54, 60, 777, 778, 514/965; 426/3, 658; 424/469, 48, 440; 127/29

[56] References Cited

U.S. PATENT DOCUMENTS

| | | | |
|---|---|---|---|
| 3,200,039 | 8/1965 | Thompson, Jr. | 424/469 |
| 4,252,794 | 2/1981 | DuRoss | 426/3 |
| 4,996,196 | 2/1991 | Mitsuhashi et al. | 426/658 |
| 4,999,058 | 3/1991 | Kawashima et al. | 426/658 |
| 5,017,400 | 5/1991 | Olinger et al. | 426/658 |
| 5,023,092 | 6/1991 | DuRoss | 127/29 |

*Primary Examiner*—Ronald W. Griffin
*Attorney, Agent, or Firm*—William E. Dickheiser

[57] ABSTRACT

A pharmaceutical composition comprising a crystalline sugar alcohol derived from at least one mono- or polysaccharide having uniformly dispersed within its crystal matrix particles of at least one pharmaceutically active compound is disclosed. Also disclosed is a method of producing such a uniformly dispersed pharmaceutical composition by the controlled crystallization of the molten sugar alcohol having the pharmaceutically active material dispersed therein.

13 Claims, No Drawings

CRYSTALLINE SUGAR ALCOHOL CONTAINING UNIFORMLY DISPERSED PARTICULATE PHARMACEUTICAL COMPOUND

FIELD OF THE INVENTION

This invention relates to a pharmaceutical composition comprising crystalline sugar alcohol derived from at least one mono- or polysaccharide having uniformly dispersed within its crystal matrix particles of at least one pharmaceutically active compound, as well as to a method of producing such a uniformly dispersed pharmaceutical composition.

BACKGROUND OF THE INVENTION

Many active pharmaceutical compounds may only be beneficially employed within very specific dosage ranges, with ineffective or even deleterious effects being encountered if too high or too low a dosage is employed. Accordingly, it is necessary that such compounds be formulated in a uniform manner such that a consistent dosage of such active compound can be readily manufactured and administered.

Particular problems exist with respect to the formulation of actives which are in the form of fine powders. These actives are typically blended with excipients employing wet granulation techniques wherein such ingredients are utilized in the form of a wet paste. The paste is blended with the pharmaceutically active powder, then dried, ground and tableted. However, such wet granulation processes are disfavored by the pharmaceutical industry because they are labor intensive, require special equipment and are highly susceptible to contamination. Moreover, it is especially difficult to employ these wet techniques for the formulation of actives, such as phenylpropanolamine and the like, which have a low bulk density and tend to be difficult to uniformly disperse in the wet granulation.

While it would be more economical to dry blend the active particulate material with powdered excipient and directly form tablets therefrom, the low levels of the particulate incorporated and the fine particle size thereof makes uniform blending exceptionally difficult. Specifically, because of such factors, separation of the active particulate from the excipient mass can occur during the granulation, blending and/or tableting process with the result that the manufactured products do not meet uniform assay requirements.

In order to minimize the segregation problem, pharmaceutical manufacturers have tried increasing the particle size of active materials by encapsulating such actives in gelatin or other film formers in addition to fats as well as by pregranulating the active with an excipient prior to formulating and tableting. However, neither encapsulation nor pregranulation may effectively prevent segregation as in many instances separation may occur upon the grinding or milling of such encapsulates or pregranulates. Moreover, these processes increase the number of formulating steps required and thus involve the incurring of additional expense.

Thus, it would be desirable to possess a pharmaceutical composition which contains a uniform concentration of particulate active material, which composition can be easily and inexpensively manufactured with low risk of contamination.

Accordingly, it is an object of this invention to provide a pharmaceutical composition having a uniform dispersion of particulate active material.

It is a further object of this invention to provide a process for economically preparing a pharmaceutical composition having a uniform dispersion of particulate active material.

The above objects and other additional objects will become more fully apparent from the following description and accompanying Examples.

SUMMARY OF THE INVENTION

In one aspect, the present invention is directed to a pharmaceutical composition comprising at least one crystalline sugar alcohol derived from a mono- or polysaccharide having uniformly dispersed within its crystal matrix particles of at least one pharmaceutically active compound.

In another aspect, this invention is directed to a process for producing a pharmaceutical composition having uniformly dispersed particulate pharmaceutically active compound therein comprising the steps of:

(A) forming a molten sugar alcohol derived from at least one mono- or polysaccharide;

(B) dispersing particles of at least one pharmaceutically active material in said molten sugar alcohol under conditions such that a homogeneous mixture is formed;

(C) cooling said homogeneous molten mixture under agitation until a viscous mass is formed; and (D) cooling said mass slowly until the sugar alcohol becomes fully crystallized.

DESCRIPTION OF THE PREFERRED EMBODIMENTS

The pharmaceutical compositions of this invention are comprised of at least one crystalline sugar alcohol derived from a mono- or polysaccharide having at least one particulate pharmaceutically active compound uniformly dispersed within its crystal matrix.

The sugar alcohols which may be employed in the practice of this invention are well known to those of skill in the art and are typically produced by the catalytic hydrogenation of mono- and/or polysaccharides derived from carbohydrates which are high molecular weight polymers derived from pentose and hexose units. Illustrative of such saccharide materials are sugars, such as dextrose and maltose; cellulose; starch; and wood sugars. These materials are typically hydrolyzed under aqueous conditions utilizing enzymes or mineral acids to form monoses, dioses and trioses, etc., which are then catalytically reduced with hydrogen by well known methods. The aqueous solutions of these sugar alcohols formed thereby are then typically treated with ion exchange resins, activated carbon, or the like to form clear solutions.

Illustrative of the sugar alcohols which may be employed in the practice of this invention are mannitol, sorbitol, maltitol, cellobiitol, lactitol, xylitol or a blend of polyols known in the art as hydrogenated starch hydrolysates. The preferred sugar alcohols are sorbitol, and blends of sorbitol with mannitol. When blends of these alcohols are employed, preferably between about 5 and about 15 weight percent mannitol and between about 85 and about 95 weight percent sorbitol are present.

The sugar alcohols employed herein generally are dried such that they have a water content of less than about 3 percent by weight. Preferably such water content is less than about 1 percent, and most preferably is less than about 0.5 percent by weight. The sugar alcohol starting materials may be dried to the desired water content by conventional means such as a continuous thin film evaporator or a batch vacuum cooker.

As is employed herein the term "pharmaceutically active compound" refers to an organic or inorganic orally ingestable compound which is taken for medicinal, dietary and/or nutritional purposes, and which is particulate in form. Illustrative of the pharmaceutically active compounds which may be beneficially formulated by the practice of this invention are organic compounds such as aspirin, cimetidine, ibuprofen, atenolol, aspartamine, saccharine, acetaminophen, phenylpropanolamine hydrochloride and the like as well as inorganic compounds such as salts and oxides of alkali metals, alkaline earth metals and mineral supplements of iron, copper and zinc, and the like.

The pharmaceutically active compounds employed in the practice of this invention are particulate in form—i.e., they are fine solids at ambient temperatures. The maximum particle size of such materials depends upon whether such materials are soluble in molten sugar alcohol, are liquids at molten sugar alcohol temperatures, or whether such compounds remain as insoluble solids in the molten sugar alcohol mass. In the former two cases, maximum particle size is not critical as large starting particles will still be dispersed easily and uniformly. However, in the latter case, it is preferred that the particle size of the pharmaceutically active compound not exceed about 500 microns, and is more preferably not in excess of about 300 microns.

Depending upon the nature and particle size of the pharmaceutically active particle employed, it is possible to uniformly formulate up to about 30 percent or more by weight of pharmaceutically active compound in the sugar alcohol excipient following the process of this invention.

The pharmaceutical composition of this invention is prepared by:

(A) forming a molten sugar alcohol derived from at least one mono- or polysaccharide;

(B) dispersing particles of pharmaceutically active material in said molten sugar alcohol under conditions such that a homogeneous mixture is formed;

(C) cooling said homogeneous molten mixture under agitation until a viscous mass is formed; and (D) cooling said mass slowly until the sugar alcohol becomes fully crystallized.

In step (A), one of ordinary skill in the art can easily determine suitable operating temperatures by routine experimentation. Typical operating temperature ranges for the following exemplary sugar alcohols are as follows: sorbitol, between about 86° and about 130° C.; mannitol, between about 80° and about 120° C.; xylitol, between about 140° and about 190° C.; maltitol, between about 100° and about 150° C.; lactitol, between about 100° and about 200° C.; cellobiitol, between about 100° and about 175° C.; and hydrogenated starch hydrolysate between about 150° and about 200° C. It should be noted, however, that the deactivation temperature of any particular pharmaceutically active compound must be taken into account when selecting the appropriate sugar alcohol to be employed, as well as the specific temperature within the acceptable operating temperature range for a given sugar alcohol.

In step (B) of the process hereof the pharmaceutically active particles are dispersed in the molten sugar alcohol under conditions such that a homogeneous mixture is formed. Should this step involve the dispersion of pharmaceutically active particles which remain as discrete solids under the operation conditions selected, any one of several techniques may be employed. For example, the molten polyhydric alcohol may be contained in a heated kettle equipped with a high shear mixing device used to create a vortex in the molten material. The particulate active ingredient may be added gradually to the vortex and agitation continued until such active is uniformly dispersed throughout the molten alcohol. In other instances, it may be preferred in certain instances to dry-mix a portion of the finely divided sugar alcohol with the particulate active in a ball mill or V-blender to create a uniform dry blend which is then added to the molten material.

For those pharmaceutically active compounds which are either soluble in the molten sugar alcohol or which are liquid at the operating temperature any conventional addition technique may be employed. Care must be taken, however, to ensure that agitation continues at the elevated temperature of the molten alcohol until complete dissolution or melting and thorough dispersion of the active compound in the molten sugar alcohol has occured.

Once the pharmaceutically active compound has been uniformly dispersed in the molten alcohol (which point can be readily determined by routine assay for any particular additive/molten alcohol combination), the temperature is reduced while agitation continues. Such cooling with agitation results in the onset of crystallization. Agitation should be continued until the formulation becomes a viscous mass. By the term "viscous mass" is meant a composition which has a semi-solid, dough-like appearance: is extrudable; and is not liquid and runny. Typically, at this point the sugar alcohol is generally at least about 40 percent crystalline by weight. However, where high loadings of active material are present, a viscous mass may be present where as little as only 20 weight percent of the sugar alcohol has crystallized. If desired, the dispersion may be periodically monitored, e.g., by differential scanning calorimetry, until the required percentage crystallinity for a given sugar alcohol/pharmaceutically active compound mixture (which percentage can easily be determined by running trials at various times until a suitable viscous mass is formed and then determining the crystallinity of such viscous mass, e.g. by differential scanning calorimetry) is observed.

The viscous mass is removed from the agitating means and allowed to further cool until a solid crystalline mass having a uniform dispersion of particulate pharmaceutically active composition is obtained. While the mixture can fully crystallize under agitation, this is generally not preferred as such solid material may block up the reactor and even damage the agitation means employed.

The fully crystalline mass may be ground, employing conventional grinding equipment, to provide a powder which can be formed into tablets or blended with additional excipients and formulated into chewing gums, tablets, and the like.

Large scale preparations may preferably be made employing a process wherein the sugar alcohol, preferably sorbitol or a blend of sorbitol and mannitol, is heated to a temperature of between about 80° C. and about 100° C. and subjected to agitation in a heated tank. After addition of the pharmaceutically active compound, under continuous agitation, the reaction mass is then metered into a continuous twin shaft mixer of the intermeshing type. Mixers of this type are discussed in "Chemical Engineers Handbook", 5th Edition, edited by R. H. Perry and C. H. Chilton (1973) pages 19-21. Characteristics of these mixers are that they include intermeshing kneader blades mounted on two parallel shafts which rotate in the same direction at the same speed with close blade-to-wall and blade-to-blade clearances.

A preferred continuous mixer is the high shear Readco Continuous Processor made by Teledyne Readco of York, Pa. The mixer shown U.S. Pat. No. 3,419,250 and in U.S. Pat. No. 3,618,902 (both assigned to Teledyne Inc.) can be used without modification; however, the sugar alcohol magma which is formed in the present process is much more easily handled if the mixer is equipped with an extrusion nozzle or plate. Other high shear continuous twin screw mixers which impart a high shearing force at low shaft speed to the material being processed can also be used. Such mixers include the Baker, Perkins Multi-Purpose (M-P) mixer made by Baker, Perkins Inc. of Saginaw, Mich., and the ZSK Twin Screw Compounding Extruder made by Werner and Pfleiderer Corporation of Stuttgart, Germany. The Baker, Perkins mixer is shown in U.S. Pat. Nos. 3,195,868 and 3,198,491. Alternative blade configurations can be used in mixers of this type are shown in U.S. Pat. Nos. 3,423,074 (assigned to Baker, Perkins) and 3,490,750 (assigned to Teledyne, Inc.). These mixers are available in various diameters and horse power ratings depending on the throughput required.

Preferably, a Readco Continuous Processor with kneader blade diameters of 5, 15 or 24 inches with feed and/or discharge screws is utilized. Further, the discharge nozzles are preferably provided with heating means in order that the surface of the partially solidified cylindrical ribbon of exiting magma does not prematurely crystallize ensuring a smooth discharge. Thus, one process for producing the pharmaceutical compositions of this invention involves continuously introducing a feed comprising the molten magma containing the added pharmaceutically active compound into an elongated mixing zone having shaft means and a plurality of kneader blades mounted on the shaft means, the configuration of the kneader blades being such as to provide restricted clearances between the blades and the adjacent walls; simultaneous cooling and kneading the molten alcohol magma as it passes through the mixing zone until a viscous mass of molten sugar alcohol and active is obtained; and continuously discharging the blend from the mixing zone through an extrusion orifice and further cooling the blend to ambient temperature forming the crystalline sugar alcohol containing included particulate.

In carrying out the crystallization, the molten sugar alcohol is preferably held in an agitated feed tank in a relatively dry atmosphere to inhibit moisture pickup such that the moisture content does not exceed about 1% by weight. This precaution becomes less of a factor as the temperature of the molten alcohol mix exceeds 100° C. At this point, the active particulate is added under agitation (e.g., high shear mixing) blended with some of the crystalline polyol, or with melted polyol or melted and/or dispersed in molten polyol, depending on the melt temperature of the polyol as well as on the specific physical characteristics of such active material. In the operation of the mixing equipment, the feed rate and other operating parameters are adjusted such that as the cooling mass passes through the mixer, a molten blend having increased concentrations of crystals is generated as the magma passes through from the feed to the discharge orifice. The rotating screws move the molten magma containing crystals and dispersed particulate active from the center of the equipment to the outer cooled edge whereupon additional crystals are precipitated and remixed with additional molten alcohol and particulate to act as a crystallizing seed. As the temperature profile drops from molten feed temperature to discharge temperature, the viscosity of melt increases due to the formation of the crystals. The action of the rotating screws pushes the crystallizing molten magma containing dispersed ingredient in the form of extrudate through the discharge orifice whereupon it is extruded as an elongated mass. The extrudate may then be conveniently cut into desired lengths and permitted to cool until crystallization is complete.

Care should be taken to ensure that the temperature of the emitted extrudate is not too hot, as the molten mass will lose its shape. Not only is such material difficult to handle, but the product obtained may be an undesirable mixture of crystals and amorphous sugar alcohol glass, having a nonuniform dispersion of the active material therein. The problem can be corrected by decreasing the throughput time or jacket cooling temperature and other variables such as feed temperature, rotation speed, back pressure, etc. Under ideal operating conditions, the extrudate crystalline paste develops a solid outer shell of crystalline product which is only slightly wetter on the interior side with molten material. The hot extrudate when permitted to stand will fully crystallize, typically over a period of between about 6 and about 96 hours depending on the cross-sectional dimension of the extrudate mass (which generally ranges in cross-section from about 5 to about 20 millimeters) and the effect of the added ingredient. Longer periods may be required for extruded shapes having a cross-sectional dimension of greater than 20 millimeters.

EXAMPLES

The following Examples are intended to further illustrate the invention and are not intended to limit the scope of the invention in any matter whatsoever. In such Examples, all proportions expressed are by weight unless otherwise specified.

EXAMPLE 1

Into a 60 gallon steam heated, agitated tank were placed 200 parts of a 70% aqueous solution of sorbitol. Under agitation, the tank was evacuated to 25 mmHg and gradually heated to 120° C. until no water was collected in the condenser. The molten material contained <0.3% by weight water. 14 parts of phenylpropanolamine hydrochloride in powder form were slowly added to the molten sorbitol at 108° C. under agitation. After mixing for a period of 25 minutes, the temperature of the molten mix was raised to 140° C. and metered from the mixing tank through a positive displacement pump into a laboratory size Readco mixer having counter-rotating mixing blades 2 inches in diameter and a barrel length of 18 inches. The mixer, jacketed with cooling water at 14°-17° C., was continuously fed at rates ranging from 32 lbs. per hour at a blade rotation speed of 200 RPMs up to 51 lbs. per hour at blade speeds of 126 RPMs. The temperature of product exiting the mixing device ranged from 88°-90° C. The exiting material was extruded through a 0.5 inch (1.27 cm) orifice into elongated strips onto a cooled moving stainless steel belt and cut into lengths ranging from 1 to 3 inches. The product coming off the moving cooling belt was placed in storage trays to cool to room temperature in a dry atmosphere for a period of 24 hours, then placed in sealed containers.

Samples taken after 5, 10, 15 and 20 minutes of operation were ground into powder using a Waring blender. The powered composition was passed through a set of stainless steel screens collecting the material passing through a 40 mesh (U.S. Sieve Series) screen and held on a 100 mesh screen (−40/+100 cut). Powder from each sample was formulated into tablets each containing a calculated content of 10 mg of phenylpropanolamine HCl by first mixing with 0.5 parts magnesium stearate in a V-blender and subsequent tableting in a Key DC16 tablet press using ⅜ inch flat faced bevel edged punches. Three tablets were chosen at random from each sample and were analyzed for their PPA content by chromatography (HPLC). The results of such assay are presented in Table I below.

TABLE I

| | mg Phenylpropanolamine HCl Per Tablet | | | |
|---|---|---|---|---|
| | Time After Operation Began (min.) | | | |
| Tablet | 5 | 10 | 15 | 20 |
| 1 | 10.91 | 9.42 | 9.70 | 10.28 |
| 2 | 9.49 | 9.42 | 9.70 | 9.62 |
| 3 | 10.37 | 9.80 | 9.63 | 10.31 |
| Mean | 10.26 | 9.56 | 9.67 | 10.07 |
| Standard Deviation | ±0.72 | ±0.21 | ±0.04 | ±0.37 |

The above data shows the uniform dispersion of phenylpropanolamine HCl achieved utilizing the process of this invention.

EXAMPLE 2

Co-Crystallized Sorbitol with Powdered Dye

A. To 6,000 grams of molten sorbitol with a moisture content of less than 0.5% held at 198° F.–205° F. (92°–96° C.) (on a hot plate), were added slowly 1.2 grams of yellow 5 dye (Warner Jenkinson). A propeller agitator immersed in the molten sorbitol created a vortex in the molten sorbitol which facilitated uniform addition of the powdered dye to the molten sorbitol. The dye wet out quickly and a very uniform color was stained in the molten polyol.

The dyed molten sorbitol was transferred to a Readco Sigma Blade 58 mixer equipped with a jacket through which 160° F. (71° C.) H₂O was circulated to keep the molten sorbitol from super cooling. The mixer was turned on and the blades, rotating at 30 RPM, agitated the molten sorbitol until crystallization was initiated as a function of such cooling and agitation. The mixer was allowed to run until the crystallizing, dyed sorbitol had transformed itself into a "dough like" viscous mass, at which time it was removed from the mixer and allowed to crystallized fully at ambient conditions [72° F. (22° C.)48% relative humidity] overnight.

The crystallized yellow sorbitol was uniform in color on observation after 12 hours. The crystallized dyed polyol was ground down using a laboratory granulator to a −40/+120 mesh cut.

To 3970 grams of the −40/+120 mesh cut of dyed (yellow 5) sorbitol were added 30 grams of magnesium stearate and the dyed sorbitol/magnesium stearate mixture was blended in a V-blender for 3 minutes, removed and tableted on a Stokes B-2 Tablet press. Tablets, 0.5 grams in weight were made using ¼ inch (0.635 cm) flat faced beveled end ("FFBE") punches at 3.0 tons pressure. Tablets were collected at 0, 5, 10 and 15 minute intervals and the color of the tablets was observed to be uniform. No segregation of granulation—which would be manifested by increased mottling—was observed in the granulation itself, the feed frame on the press, or in the tablets themselves.

B. To 3,000 grams of molten sorbitol were added 0.6 grams of Yellow 5 dye in addition to 30 grams of cimetidine. Both the dye and the cimetidine were added to the molten sorbitol at a vortex produced by an agitator. Agitation was for 10 minutes at 190° F. (88° C.) in order to thoroughly incorporate the dye/active.

The mass was crystallized and ground to −40/+120 mesh as described in Example 2A above. To 992.5 grams of the ground sorbitol/cimetidine powder were added 7.5 grams of magnesium stearate. The mixer blended for 3 minutes in a V-blender, and tablets made on a Stokes press using 3 tons pressure, ¼ inch (0.635 cm) FFBE edge punches, producing 0.5 gram tablets using 2 stations on the press.

Tablets were produced from random samples after 0, 5 and 10 minutes of running. The tablets were observed to be very uniform in color. No segregation was noted either in the granulations, the feed frame, or the tablets.

EXAMPLE 3

Phenylpropanolamine hydrochloride/Sorbitol

Into a jacketed stainless steel reactor heated to 110° C. were added 46.2 parts of molten sorbitol syrup with a moisture content of 0.2%. A high shear mixer was placed in the molten sorbitol and sufficient agitation was provided to produce a vortex while adjustment was made to the temperature control of the jacket to compensate for the "cooling" of the melt due to the agitation and incorporation of cooler ambient air. With the temperature of the molten sorbitol stabilized at 110° C. +/−10° C. to prevent premature crystallization, 7.6 parts of a 1:1 blend of phenylpropanolamine hydrochloride (PPH) (mp 190°–194° C.) and crystalline sorbitol (gamma polymorph) powder (which had been previously dry blended in order to increase the dispersion rate of the phenylpropanolamine hydrochloride in the sorbitol as PPH tends to "float" when added to molten sorbitol) were slowly added to the vortex to maximize shear and ensure uniform distribution in the melt. Upon stabilization of the phenylpropanolamine dispersion at a temperature of 110° C. with the agitator turning at 90 r.p.m., another 46.2 parts of molten sorbitol heated at 110° C. were added.

Once thoroughly dispersed, the molten sorbitol melt containing uniformly dispersed particles of phenylpropanolamine hydrochloride was placed in a jacketed agitator equipped with double Sigma blades and slowly cooled to 90° C. with a steam/water mix flowing through the jacket and maintaining constant agitation, until the molten magma was crystallized to a viscous mass. At this point, such viscous mass was transferred to trays and held in an oven at 90° C. for 4 hours until it was fully crystallized. Lumps of this fully crystallized material were ground in a Waring blender and screened through a set of stainless steel screens collecting the material passing through the 40 mesh (U.S. Sieve Series) screen and held on a 100 mesh screen (−40/+100 cut). The resultant powder was assayed and was found to contain 3.8% phenylpropanolamine hydrochloride.

EXAMPLE 4

Sodium Fluoride/Sorbitol

Five parts sodium fluoride powder were added to 95 parts molten sorbitol which had been heated to a temperature of 110° C. in a stainless steel mixer. The fluoride was added slowly to the sugar alcohol melt under high speed, high shear agitation and thereafter mixed for an additional 10 minutes. This melt containing 5% sodium fluoride was transferred to a jacketed Sigma blade mixer heated to about 75° C. with hot water passing through the jacket. The melt was agitated in the mixer for about 30 minutes at 30 r.p.m. until it partially crystallized. The partially solidified viscous mass was removed from the mixer and placed in trays to allow it to crystallize fully while held at a temperature of 100° C. for 24 hours. Samples of this material were ground in a laboratory Waring blender and screened to collect a −40/+100 fraction.

The ground, screened material containing 5% sodium fluoride was mixed with 0.75% magnesium stearate in a V-blender for 3 minutes and the granulation was fed to a Stokes B-2 rotary press set up to produce a 3/16" concave faced tablet weighing 0.2 grams with a 5 kg Strong Cobb hardness. There was no sticking to the punch faces or die side walls. The tablets possessed a white, shiny, glossy surface with a smooth, elegant texture.

EXAMPLE 5

Cimetidine/Sorbitol 474 parts of anhydrous sorbitol were melted in a stainless steel reactor equipped with agitation means and heated to a temperature of 105° C. The molten sorbitol was agitated at a speed of 100 r.p.m. to create a vortex and thereafter 25 parts of cimetidine (melting point 141°-143° C.) were added to the vortex slowly to avoid forming lumps. After complete addition, the melt was agitated for an additional 10 minutes. This melt was transferred to a Sigma blade mixer heated at 90° C. with hot water and agitated at 18 r.p.m. After 1 minute of mixing, 1% crystalline sorbitol seed fines (less than 325 mesh) were slowly added over the surface of the agitating melt to achieve a uniform dispersion of the seeds in the melt in order to initiate a rapid crystallization in the mixer. When the crystallizing mass achieved a dough-like consistency in the mixer, it was removed and placed on a tray, spread out and placed in an oven at 50° C. for 10 hours until it was fully crystallized. The crystalline mass was cooled and aggregates of the material were ground in a laboratory Waring blender (medium speed, 5 seconds), then screened to collect a −40/+100 mesh fraction.

Tablets of this material were made by combining 198 grams of the screened material with 2 grams of magnesium stearate in a rotating jar for 3 minutes. Using a Stokes B-2 press, uniform tablets containing 5% cimetidiene having a weight of 0.3 grams and a Strong Cobb hardness of 5 kg were produced. These tablets had a smooth texture and did not produce astringency in the mouth when chewed. By comparison, dry blends of cimetidine with sorbitol powder which were thereafter tableted were very bitter and left an astringent aftertaste. No problems with sticking or picking in the dyes or on the punches was encountered in the Stokes press.

EXAMPLE 6

Ibuprofen/Sorbitol 950 parts of a sorbitol were heated in a stainless steel mixer to 110° and then slowly cooled under high speed agitation to 75° C. and maintained at that temperature. 50 parts of ibuprofen (mp 75°-77° C.) were added very slowly to the vortex to ensure a homogenous distribution. After mixing for 10 minutes, the melt containing 5% ibuprofen was transferred to a Sigma blade mixer and the temperature maintained at 74° C., while agitation continued for 20 minutes at a rotation speed of 30 r.p.m. until the mixture partially crystallized. The partially solidified mass was removed from the mixer and placed on a tray to allow it to crystallize fully while held at a temperature of 50° C. for 12 hours. The material was cooled and ground and screened to produce a particle size distribution of −40/+100.

99 parts of the finely divided material were mixed with 1 part magnesium stearate in a V-blender for 3 minutes, and the mixture was tableted in a Stokes B-2 rotary press to produce tablets having a bisect weighing 0.7 gm with a Strong Cobb hardness of 7 kg. These tablets had a smooth, elegant texture on chewing with no discernible grit.

Tablets containing 10% ibuprofen were made by a similar procedure by mixing 10 parts of active with 90 parts molten sorbitol/mannitol at 75° C. No sticking or picking was noted in the tablet press. The tablets were smooth and chewable but more bitter than those containing 5%. The tablets were significantly better in taste and quality than those produced by tableting pure ibuprofen powder with crystalline sorbitol powder.

EXAMPLE 7

Phenylpropanolamine Hydrochloride 50 parts of PPH were added directly to 450 parts of molten sorbitol and processed in accordance with the method described in Example 1. The crystallized product was ground and screened through a −20/+100 set of stainless steel screens. The average analysis for this material was 10% by weight active.

Three granulations were prepared to produce tablets with 10% +−0.5%, 5% and 2.5% active by blending with Crystalline Sorbitol 1162 (provided by ICI Americas Inc.). The 5% and 2.5% tablets were made by blending pure crystalline sorbitol in a ratio to product the desired dilution of active in the formulation by blending with the powder of 10% active material along with 0.5 parts magnesium stearate per 100 weight in a V-blender. The three concentrations were tableted in a Key DC16 tablet press using ⅝" flat faced, bevel edged punches to make one gram tablets at three tons pressure. The tablets were made without lamination or capping and had a smooth texture. The tablets had a hardness (Strong Cobb) of 16-18 kg and a friability less than 0.2 gm.

What is claimed is:

1. A pharmaceutical composition comprising crystalline sugar alcohol derived from at least one mono- or polysaccharide having uniformly dispersed within its crystal matrix particles of at least one pharmaceutically active compound.

2. A composition in accordance with claim 1 wherein said sugar alcohol is selected from the group consisting of sorbitol, mannitol, co-crystallized sorbitol with mannitol. xylitol. maltitol. lactitol. cellobiitol and hydrogenated starch hydrolysates.

3. A composition in accordance with claim 1 wherein said sugar alcohol is sorbitol.

4. A composition in accordance with claim 1 wherein said sugar alcohol is co-crystallized sorbitol and mannitol.

5. A composition in accordance with claim 4 wherein said sugar alcohol contains between about 5 and about 15 percent by weight mannitol.

6. A composition in accordance with claim 1 wherein said pharmaceutically active compound is selected from the group consisting of oxides and salts of alkali and alkaline earth metals; mineral supplements of iron, manganese. copper and zinc; aspartamine; saccharine; phenylpropanolamine HCL; ibuprofen; cimetidine; atenolol; acetaminophen; and aspirin.

7. A composition in accordance with claim 1 wherein said composition is in the form of a tablet.

8. A composition in accordance with claim 1 wherein said composition is in the form of chewing gum.

9. A process for producing pharmaceutical compositions having uniformly dispersed particulate actives comprising the steps of:
(A) forming a molten sugar alcohol derived from at least one mono- or polysaccharide;
(B) dispersing particles of at least one pharmaceutically active material in said molten alcohol under conditions such that a homogeneous mixture is formed;
(C) cooling said homogeneous molten mixture while agitating until a viscous mass is formed; and
(D) cooling said mass slowly to a point where said alcohols become fully crystallized.

10. A process in accordance with claim 9 wherein the active material remains as a discrete particle within the molten alcohol.

11. A process in accordance with claim 10 wherein in step B the active material is added in the form of a preblend with powdered sugar alcohol.

12. A process in accordance with claim 9 wherein the active material is dissolved in the molten alcohol.

13. A process in accordance with claim 9 wherein the active material melts in the molten alcohol.

* * * * *